United States Patent [19]

Wellner

[11] Patent Number: 5,008,372

[45] Date of Patent: Apr. 16, 1991

[54] DEBLOCKING AMINO TERMINAL N-ACETYL SERINE AND N-ACETYL THREONINE RESIDUES IN PEPTIDES AND PROTEINS TO ALLOW SEQUENCING

[75] Inventor: Daniel Wellner, New York, N.Y.

[73] Assignee: Cornell Research Foundation, Inc., Ithaca, N.Y.

[21] Appl. No.: 478,917

[22] Filed: Feb. 12, 1990

[51] Int. Cl.$^5$ .................. C07K 3/08; C07K 15/00; G01N 33/68

[52] U.S. Cl. .................. 530/345; 435/177; 435/188; 436/89; 436/90; 530/337; 530/410

[58] Field of Search .................. 436/89, 90; 530/345, 530/337, 410; 435/177, 188

[56] References Cited

U.S. PATENT DOCUMENTS

| | | | |
|---|---|---|---|
| 3,717,436 | 2/1973 | Penhasi | 436/89 |
| 3,959,307 | 5/1976 | Wittmann | 548/309 |
| 4,065,412 | 12/1977 | Dreyer | 525/54.1 |
| 4,153,416 | 5/1979 | Bonner | 436/57 |
| 4,155,714 | 5/1979 | Bonner | 530/333 |
| 4,548,904 | 10/1985 | Kent | 436/89 |
| 4,665,037 | 5/1987 | Stolowitz | 436/89 |
| 4,701,419 | 10/1987 | Morris | 436/89 |
| 4,704,256 | 11/1987 | Hood | 422/68 |
| 4,745,178 | 5/1988 | DiMardi et al. | 530/410 |
| 4,782,139 | 11/1988 | DiMarchi et al. | 514/21 |
| 4,861,726 | 8/1989 | Stolowitz | 436/89 |
| 4,863,870 | 9/1989 | Stolowitz | 436/89 |

OTHER PUBLICATIONS

Clinton, M., et al., Biochem. Biophys. Res. Commun. 158, pp. 855–862, (1989).

Pannerselvam, C., Biochem, Biophys, Res. Commun. 155, pp. 539–545, (1988).

Roesijadi, G., et al., Archives of Biochemistry and Biophysics, vol. 273, No. 2, 403–413, (9/89).

Primary Examiner—Howard E. Schain

[57] ABSTRACT

Deblocking of amino terminal N-acetyl serine and N-acetyl threonine residue in proteins and peptides to allow sequencing by the Edman degradation technique is carried out by reacting blocked protein or peptide with anhydrous trifluoracetic acid for 1 to 15 minutes at 30° to 60° C., removing the remaining trifluoroacetic acid and maintaining reacting mixture from which trifluoroacetic acid has been removed at 30° to 100° C. for 60 minutes to 5 days.

6 Claims, No Drawings

DEBLOCKING AMINO TERMINAL N-ACETYL SERINE AND N-ACETYL THREONINE RESIDUES IN PEPTIDES AND PROTEINS TO ALLOW SEQUENCING

This invention was made at least in part with Government support under a Biomedical Research Support Grant 2 S07RR05396 and a Grant SIORR02855-01, and a Grant AGQ0541-13 (Project 4) and a Grant 5 RO1 A122901-03 all from the National Institutes of Health.

TECHNICAL FIELD

This invention is directed at deblocking of blocked N-terminal amino acid residues in proteins and peptides which prevent sequencing by Edman degradation.

BACKGROUND OF THE INVENTION

An important method for determining the sequence of amino acids in proteins and peptides is known as the Edman degradation process. This process was first described in Edman, P., Acta Chem. Scand. 4, 283(1950). The process involves coupling the N-terminal amino acid of the protein or peptide in a basic environment to phenylisothiocyanate (PITC) to form phenylthiocarbamyl (PTC) derivative, then cleaving the PTC derivative using anhydrous strong acid, such as trifluoroacetic acid, to form an anilinothiazolinone (ATZ) derivative of the N-terminal amino acid and free peptide which is the original protein or peptide with the N-terminal amino acid residue removed, then converting the (ATZ) amino acid derivative to a phenylthiohydantoin (PTH) amino acid derivative which can be analyzed by chromatography and repeating the steps for each amino acid residue that becomes the terminal residue as a result of the cleavage step.

One problem frequently encountered is that the N-terminal residue is modified in such a way that it does not react with the Edman reagent, phenylisothiocyanate, that is that the N-terminal residue is blocked. The most frequently encountered blocked N-terminal residue is an N-acetylamino acid residue. Evidence has been presented that about 80% of the soluble proteins in mammalian cells have acetylated N-terminal amino acids. (Brown, J. L., et al, J. Biol. Chem. 251, 1009-1014, 1976).

The need to remove blocking groups to convert the N-terminal residue to free N-terminal amino acid before sequencing can begin is mentioned in Kent et al U.S. Pat. No. 4,548,904. Previous attempts to remove blocking groups have involved enzymatic or limited HCl hydrolysis.

Nakamura, S., et al, Biochem. Biophys. Res. Commun. 58, 250-256 (1974) report use of rat liver peptidase to remove N-acetyl serine from the N-terminal peptide released from thrombin by bovine Factor XIII. Kobayashi, K., et al, J. Biol. Chem. 262, 11435-11445 (1987) and Jones, W. M., et al, Biochem. Biophys. Res. Commun. 139, 244-250 (1986) report use of rat liver peptidase and a similar enzyme from human erythrocytes to split off N-acetyl serine from α-melanocyte stimulating hormone. However, the applicability of the enzyme deblocking method is limited by the restricted specificity of the enzymes.

Fordyce, A. M., et al, Biochem. Soc. Trans. 7, 721-723 (1979) and Chin, C.C.Q., et al, Bioscience Rep. 5, 847-854 (1985) report some success in removing N-acetyl groups from peptides by limited HCl hydrolysis. The disadvantage of this method is that other bonds may be split besides the bond between the terminal acetyl and the nitrogen to which it is attached thereby providing a plurality of different end groups.

It is an object herein to provide a method of deblocking amino terminal N-acetyl serine and N-acetyl threonine residues in peptides and proteins to allow sequencing, with improved specificity compared to enzyme deblocking and wherein the disadvantages of hydrolysis are minimized. A survey of N-acetylated proteins by Persson, B., et al, Eur. J. Biochem. 152, 523-527 (1985) found that of the known proteins in this class, about 41% have an N-terminal acetylated serine and another 2% have an N-terminal acetylated threonine.

SUMMARY OF THE INVENTION

This object and advantages as are evident below are accomplished by the method of the invention herein, which comprises the steps of:

(a) reacting the protein or peptide having N-terminal acetyl serine or N-terminal acetyl threonine residue with anhydrous trifluoroacetic acid for 1 to 15 minutes at 30 to 60° C., (b) removing the remaining trifluoroacetic acid, (c) and maintaining the reaction mixture from which trifluoroacetic acid has been removed at 30 to 100° C. for 60 minutes to 5 days.

DETAILED DESCRIPTION

Any protein or peptide with an amino terminal N-acetyl serine or N-acetyl threonine residue can be deblocked by the method herein. Persson, B., et al, Eur. J. Biochem. 152, 523-527 (1985) lists several proteins which contain an amino terminal N-acetyl serine or N-acetyl threonine residue, for which sequences have been determined. In the case of proteins or peptides for which structures are not known and where sequencing cannot be obtained by Edman degradation, eligibility of those for deblocking by the method herein to allow sequencing by Edman degradation is best determined by trying the method herein.

While the method herein is applicable to both large and small proteins and peptides in that N-terminal acetyl serine and threonine end groups are deblocked, for large proteins and peptides the background can be too high for the sequence to be clearly read. In such cases it can be advantageous to isolate an N-terminal peptide prior to deblocking and sequencing, e.g., by treating the protein with a protease to split off N-terminal fragments which are isolated by chromatography for deblocking by the method herein to provide deblocked N-terminal peptide fragments for sequencing.

The trifluoroacetic acid used in step (a) should be anhydrous to minimize the possibility of hydrolysis in the protein or peptide which is treated which can interfere with sequencing.

The trifluoroacetic acid is used in step (a) in large excess, e.g., in an amount ranging from 20 to 40,000 equivalents.

As indicated above, step (a) is carried out for to 15 minutes at 30 to 60° C. The times and temperatures are important. Shorter times and lower temperatures than those recited can result in insufficient reaction thereby depleting yields thereby decreasing the number of residues that can be sequenced. Longer times and higher temperatures than those recited can cause increase of splitting at bonds in addition to the one between the terminal acetyl and the nitrogen to which it is attached Preferably, in step (a), reaction is carried out for 2 to 5 minutes at 40 to 50° C.

While not wishing to be bound by theory, it is speculated that in step (a) reaction involves an acid catalyzed N→O shift of the acetyl group as illustrated below:

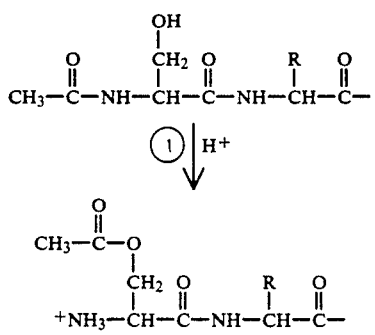

We turn now to step (b). The removal of remaining trifluoroacetic acid is carried out to terminate step (a). This step is preferably carried out by evaporating the remaining trifluoracetic acid. This evaporation is preferably carried out at room temperature, e.g., under a laboratory hood. The reaction mixture from which trifluoroacetic acid is evaporated is preferably dried before step (c) to remove any remaining traces of trifluoroacetic acid; this is readily carried out by maintaining the evaporated reaction mixture at 30 to 60° C. for 5 to 20 minutes.

We turn now to step (c). The longer the time utilized, the lower the temperature that can be utilized. The shorter the time utilized, the higher the temperature that can be utilized. Shorter times and lower temperatures than those recited can result in depleting yields. Longer times and higher temperatures than those recited can result in increase of splitting at bonds in addition to the one between the terminal acetyl and the nitrogen to which it is attached. Temperature and time combinations that have been found quite suitable are 60 to 70° C. maintained for 10 to 20 hours and 40 to 50° C. maintained for 60 to 85 hours.

While not wishing to be bound by theory, it is theorized that reaction in step (c) involves β elimination of N→O shifted acetyl as illustrated below:

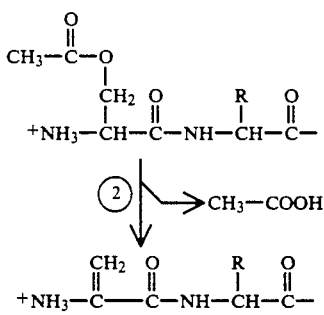

In general, the times and temperatures in steps (a) and (c) should be such that a deblocking yield (i.e., mole percent of N-terminal acetic acid removed) of at least 5% is obtained.

Sequencing can be carried out on the reaction mixture according to typical Edman degradation sequencing procedures. While not wishing to be bound by theory, it is theorized that coupling according to an Edman sequencing procedure proceeds on deblocked product as illustrated below:

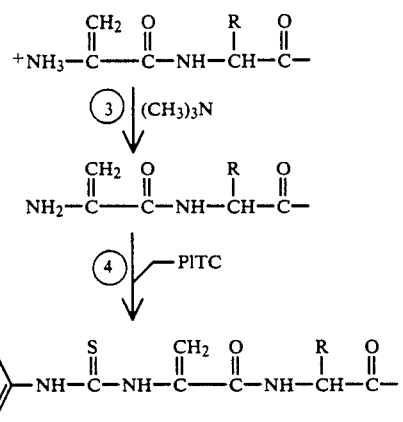

The best mode of the invention known to the inventor is illustrated by the specific working examples below.

In the examples, the following procedure was used:

A trifluoroacetic acid-treated glass fiber filter disc, 12 mm in diameter, was inserted, slightly folded, into a 1.5 ml polypropylene microcentrifuge tube. The filter was wetted with 30 μl of a solution containing polybrene (3 mg) and NaCl (0.2 mg) and dried. A solution of the protein or peptide to be tested was applied to the filter and dried. The filter was then saturated with 30 μl of anhydrous trifluoroacetic acid (Sequencer Reagent 3) and the tube closed. After incubating for 4 min. at 45° C., the tube was opened in the hood to allow most of the trifluoroacetic acid to evaporate. After 5 min. at room temperature, the open tube was allowed to dry for another 10 min at 45° C. The tube was then closed and placed in an oven at 65° C. for 16 hr. (Example II) or for times as indicated (Example III) or at 45° C. for 3 days (Example I). Sequencing was then carried out according to the manufacturer's recommendations in an Applied Biosystems gas-phase sequencer model 470A equipped with an on-line PTH analyzer model 120A. Program 03RPTH was used.

EXAMPLE I

Deblocking reaction was carried out as described above on 1.5 nmol of rat parathymosin isolated from liver by the procedure described in Komiyama, T., et al, Proc. Natl. Acad. Sci. USA 83, 1242-1245 (1986), which Komiyama, et al have shown to contain acetylated N-terminal serine. The initial yield of deblocked protein was about 7%. Sequencing results as determined for the first 7 positions are set forth in the Table I below.

TABLE I

| Position | 1 | 2 | 3 | 4 | 5 | 6 | 7 |
|---|---|---|---|---|---|---|---|
| Residue Identified | Ser | Glu | Lys | Ser | Val | Glu | Ala |
| Amount (pmol) | 97* | 115 | 55 | 87* | 47 | 54 | 50 |
| Yield (%) | 6.5 | 7.7 | 3.7 | 5.8 | 3.1 | 3.6 | 3.3 |

*Calculated from the sum of PTH-serine and the dithiothreitol adduct of PTH-dehydroalanine.

Without deblocking, sequencing cannot be determined on rat parathymosin by Edman degradation.

The same N-terminal sequence was obtained for bovine parathymosin.

The same N-terminal sequence has also been determined for human parathymosin.

Deblocking by the above procedure and sequencing was also carried out on rat prothymosin α (contains N-terminal acetyl serine) isolated from thymus glands as described in Komiyama, T., et al, Proc. Natl. Acad. Sci. USA 83, 1242–1245 (1986).

EXAMPLE II

Deblocking reaction was carried out as described above on 20 nmol of a synthetic peptide having an N-terminal acetyl threonine and having the sequence N-acetyl-thr-cys-asp-leu-ala-pro-pro-ala-gly-thr-thr. An initial yield of about 6% was obtained. A separate run carried out without deblocking showed that at least 99.5% of the peptide was blocked. The sequencing results determined are set forth in Table II below.

TABLE II

| Position | 1 | 2 | 3 | 4 | 5 |
|---|---|---|---|---|---|
| Residue Identified | Thr | Cys | Asp | Leu | Ala |
| Amount (nmol) | 0.79 | * | 0.74 | 1.07 | 1.35 |
| Yield (%) | 4.0 | — | 3.7 | 5.4 | 6.7 |
| Position | 6 | 7 | 8 | 9 | 10 | 11 |
| Residue Identified | Pro | Pro | Ala | Gly | Thr | Thr |
| Amount (nmol) | 0.90 | 1.02 | 1.10 | 0.66 | 0.41 | 0.31 |
| Yield (%) | 4.5 | 5.1 | 5.5 | 3.3 | 2.1 | 1.6 |

EXAMPLE III

Deblocking reaction was carried out as described above at times for step (c) of 1, 4, 10, 16 and 24 hours on 2 nmol of thymosin $\beta_4$ (purified from rat thymus according to the procedure described in Haritos, A. A., et al, Anal. Biochem. 144, 436–440, 1985) which is known to be a 43 residue peptide containing 3 serine and 3 threonine residues in addition to an N-terminal acetyl serine residue (Low, T., et al, Proc. Natl. Acad. Sci. USA 78, 1162–1166, 1981). An optimal yield of about 40% deblocking was obtained. Table III below sets forth the sequencing determined, the yields at two representative positions (lysine at position 3 designated "Lys-3" and proline at position 4 designated "Pro-4"), background glutamate yield in the third cycle designated "Background Glu-3 yield" indicating amount of internal cleavage during deblocking, and the ratio of ⅓ of the yield of glutamate in the third cycle to the yield of lysine in the third cycle designated "⅓ Glu-3 yield/Lys-3 yield".

TABLE III

| Incubation time at 65° C. (hr) | 1 | 4 | 10 | 16 | 24 |
|---|---|---|---|---|---|
| Lys-3 yield (%) | 4.6 | 10.0 | 10.6 | 41 | 41 |
| Pro-4 yield (%) | 5.1 | 10.1 | 10.0 | 37 | 40 |
| Background Glu-3 yield (%) | 1.8 | 2.6 | 2.5 | 18 | 9.2 |
| ⅓ Glu-3 yield/Lys-3 yield | 0.13 | 0.09 | 0.08 | 0.15 | 0.07 |

The results in Table III demonstrate an optimal yield on deblocking for about 16 hours (see yields of Lys-3 and Pro-4 at 16 hours), and assuming equal cleavage at all internal serine and threonine residues during deblocking, that the internal cleavage occurring during deblocking corresponds to about 10% of the cleavage of the N-terminal acetyl group (Table III, last line).

COMPARATIVE EXAMPLE I

When the conditions of the invention herein were carried out on heart cytochrome C, a protein with an N-terminal N-acetyl glycine, sufficient deblocking was not obtained to obtain sequencing.

Variations will be evident to those skilled in the art. Therefore, the scope of the invention is intended to be determined by the claims.

What is claimed is:

1. A method for deblocking amino terminal N-acetyl serine and N-acetyl threonine residues in proteins and peptides to allow sequencing, said method comprising the steps of:
   (a) reacting the protein or peptide having N-terminal acetyl serine or N-terminal acetyl threonine residue with anhydrous trifluoroacetic acid for 1 to 15 minutes at 30 to 60° C.,
   (b) removing the remaining trifluoroacetic acid,
   (c) maintaining the reaction mixture from which trifluoroacetic acid has been removed at 30 to 100° C. for 60 minutes to 5 days.

2. The method of claim 1 wherein in step (a) the reaction time ranges from 2 to 5 minutes and the reaction temperature ranges from 40° to 50° C.

3. The method of claim 1 wherein in step (c) a temperature ranging from 60 to 70° C. is maintained for 10 to 20 hours.

4. The method of claim 1 wherein in step (c) a temperature ranging from 40 to 50° C. is maintained for 60 to 85 hours.

5. The method of claim 1 wherein the protein or peptide in step (a) has an N-terminal acetyl serine residue.

6. The method of claim 1 wherein the protein or peptide in step (a) has an N-terminal acetyl threonine residue.

* * * * *

UNITED STATES PATENT AND TRADEMARK OFFICE
CERTIFICATE OF CORRECTION

PATENT NO. : 5,008,372

DATED : April 16, 1991

INVENTOR(S) : Daniel Wellner

It is certified that error appears in the above-identified patent and that said Letters Patent is hereby corrected as shown below:

On the cover page under "OTHER PUBLICATIONS" additionally list the following:

The Protein Society, Abstract T932
      from Program and Abstracts of
      Second Symposium, San Diego, CA
      8/13-17/1988

Hugli, T. (ed.), Techniques in Protein
      Chemistry, Academic Press,
      San Diego, CA, pp. 7-15
      (5/2/89)

Signed and Sealed this

First Day of September, 1992

Attest:

DOUGLAS B. COMER

Attesting Officer     Acting Commissioner of Patents and Trademarks